United States Patent [19]
Elliott et al.

[11] 4,342,616
[45] Aug. 3, 1982

[54] TECHNIQUE FOR PREDICTING OXYGEN PRECIPITATION IN SEMICONDUCTOR WAFERS

[75] Inventors: Brian J. Elliott, Yorktown Heights; Eric W. Hearn, Wappingers Falls; Gary Markovits, Poughkeepsie, all of N.Y.

[73] Assignee: International Business Machines Corporation, Armonk, N.Y.

[21] Appl. No.: 235,207

[22] Filed: Feb. 17, 1981

[51] Int. Cl.³ .......................................... C30B 15/20
[52] U.S. Cl. ..................................... 156/601; 324/62
[58] Field of Search .................. 156/601, DIG. 64; 324/158 D, 62 R; 29/574

[56] References Cited

U.S. PATENT DOCUMENTS 3,669,757  6/1972  Kaufmann et al. ................ 156/601
3,805,160  4/1974  Phibrick et al. ................ 324/158 D

OTHER PUBLICATIONS

Physical Review vol. 28, No. 8, pp. 882-887, 8/57 Kaiser et al.
Physical Review vol. 105, 3/15/57, pp. 1751-1756 Kaiser.
IEEE Transactions on Instrumentation and Measurement vol. 1M-13, 12/67 No. 4 pp. 323-324.

Primary Examiner—Hiram Bernstein
Attorney, Agent, or Firm—Wolmar J. Stoffel

[57] ABSTRACT

A method or technique is disclosed for predicting precisely where oxygen precipitation will occur in semiconductor wafers that are being processed in connection with integrated circuit manufacture; the technique is based upon the discovery that such precipitation will occur at resistivity peaks measured prior to any thermal treatment of the wafers. In other words, the technique permits characterizing the wafers by the diametral resistivity profile that is obtained in the initial resistivity measurements, whereby a change in oxygen precipitation can be predicted precisely where compensated intrinsic regions have been measured in the initial measurements.

4 Claims, 10 Drawing Figures

270-1
100 mm
1% DWN XTAL

OXYGEN PRECIPITATION VS. RADIUS

AFTER 30 hrs. AT 1000°C IN DRY $O_2$

270-10
100 mm
24% DWN XTAL

OXYGEN PRECIPITATION VS. RADIUS

AFTER 30 hrs. AT 1000°C IN DRY $O_2$

TECHNIQUE FOR PREDICTING OXYGEN PRECIPITATION IN SEMICONDUCTOR WAFERS

BACKGROUND OF THE INVENTION

1. Field of the Invention

This invention relates to the processing of semiconductor wafers for the purpose of producing integrated circuits and the like, and particularly to a specialized technique useful in such production.

The present invention provides a measurement technique that makes for extremely efficient processing of semiconductor wafers because it enables the prediction of their propensity for oxygen precipitation, and thereby their characterization for ultimate device purposes, prior to the application of any heat treatment that is conventionally utilized.

2. Background Art

A variety of studies have been conducted over the past thirty years or so on the various effects of oxygen as an impurity in the processes of growing semiconductor crystalline bodies. For background material reporting on such studies, reference may be made for example to an article by W. Kaiser in *Physical Review*, Vol. 105, page 1751 (1957) and to an article by Kaiser and Keck in the *Physical Review*, Vol. 28, No. 8, page 882 (Aug. 1957).

Although the aforenoted studies establish the fact that the final resistivity obtained for a substrate or crystalline body depends on the oxygen contents of that body because of the well known phenomenon of generation of thermal donors, nevertheless there has been no technique developed in the art for predicting with accuracy the final profile of oxygen precipitation that will be obtained in a given wafer.

Accordingly, it is a primary object of the present invention to provide a technique that, by resistivity measurements taken prior to any heat treatment, will enable efficient characterization of wafers.

Another object of the invention is to apply the technique in such a way as to feed back the resistivity information obtained to the crystal growing activity, whereby appropriate modifications can be made in the crystal growth operation so as to correct undesired characteristics.

Another object is to utilize the discovery of the present invention as a sorting or screening device for the manufacturing process whereby certain wafers that have undesirble characteristics can be ruled out for further processing; alternately, the technique can be employed simply to characterize the various wafers that are encountered so that they can be appropriately utilized. In other words, those wafers that would normally be ruled out for the more general case, and thereby eliminated, would instead be retained, even though they did not possess the desired uniform resistivity pattern. Thus, wafers having apparently undesirable characteristics would be classified precisely for possible later use.

SUMMARY OF THE INVENTION

In fulfillment of the previously stated objects of the present invention, a feature thereof is based on the discovery that oxygen precipitation occurs in a configuration which is predicted by the initial measurements of resistivity in a diametral pattern. In other words, one can tell from the diametral resistivity pattern obtained, the extent of the oxygen precipitation; hence whether or not a given wafer will be suitable for the conventional production line.

Accordingly, in its broadest aspect, the present invention resides in a process for selecting raw monocrystalline silicon wafers, which have been cut from a crystal body for purposes of integrated circuit manufacture, comprising the steps of measuring, prior to any thermal treatment, the resistivity at a plurality of sites along the diameter of the wafers; characterizing such wafers by the diametral resistivity profile thus obtained, according to which a change in oxygen precipitation can be predicated precisely where compensated intrinsic regions have been measured; and classifying said wafers based on the predicted oxygen precipitation characteristics. Preferably, those waters which are characterized by having substantially uniform resistivity measurements will be selected for integrated circuit manufacture; whereas the remaining wafers can be retained for use in accordance with their predicted individual oxygen precipitation characteristics corresponding with the measured compensated intrinsic regions.

DESCRIPTION OF PREFERRED EMBODIMENT

Figure 1:
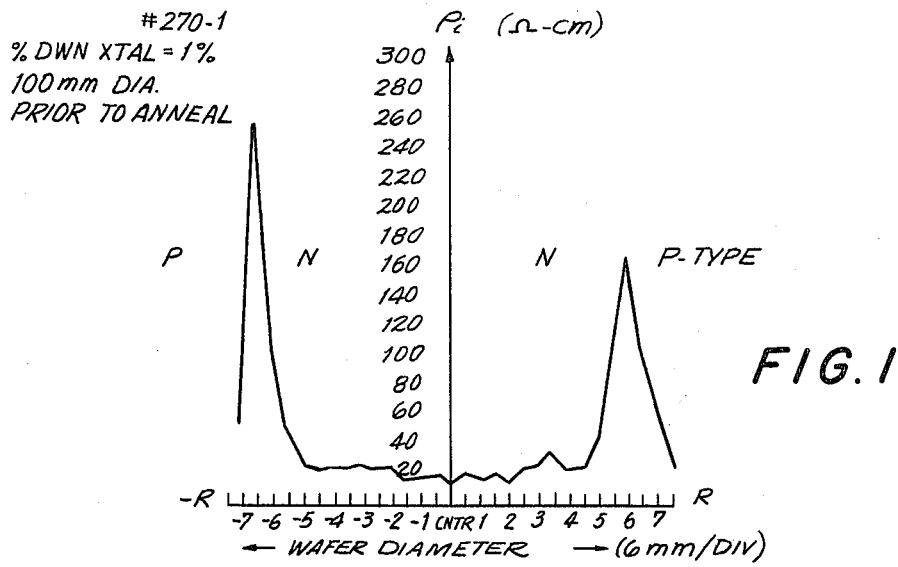
FIG. 1 is a plot of initial resistivity, measured prior to thermal donor anneal, versus wafer diameter for a first sample.
Figure 2:
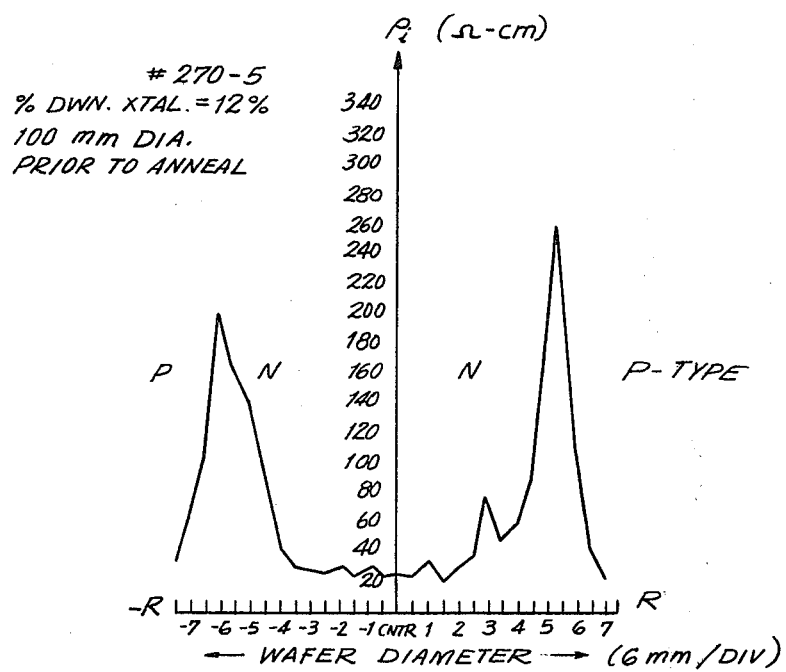
FIG. 2 is a plot similar to FIG. 1, but for a second sample.
Figure 3:
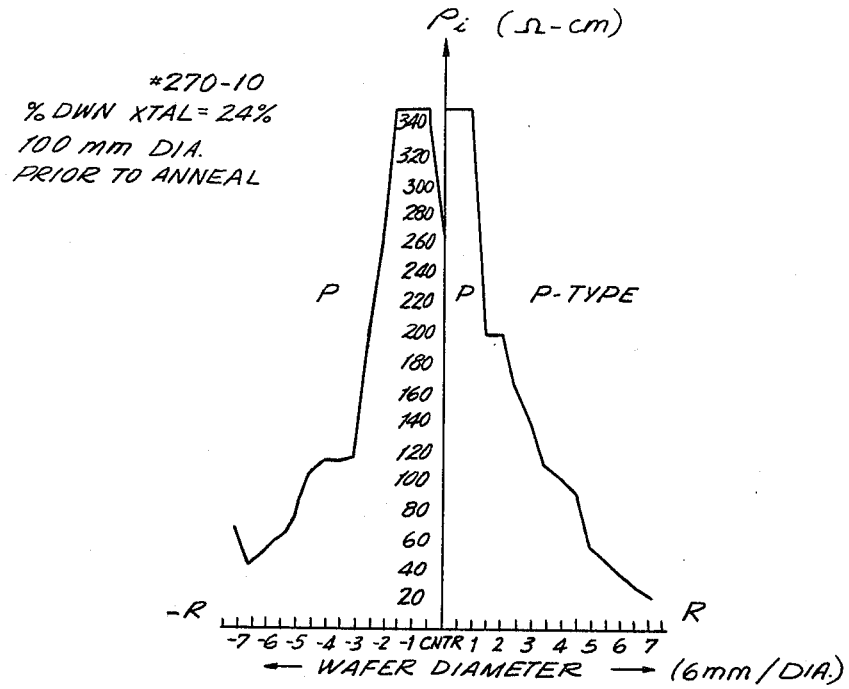
FIG. 3 is a plot similar to FIG. 1, but for a third sample.
Figure 4:
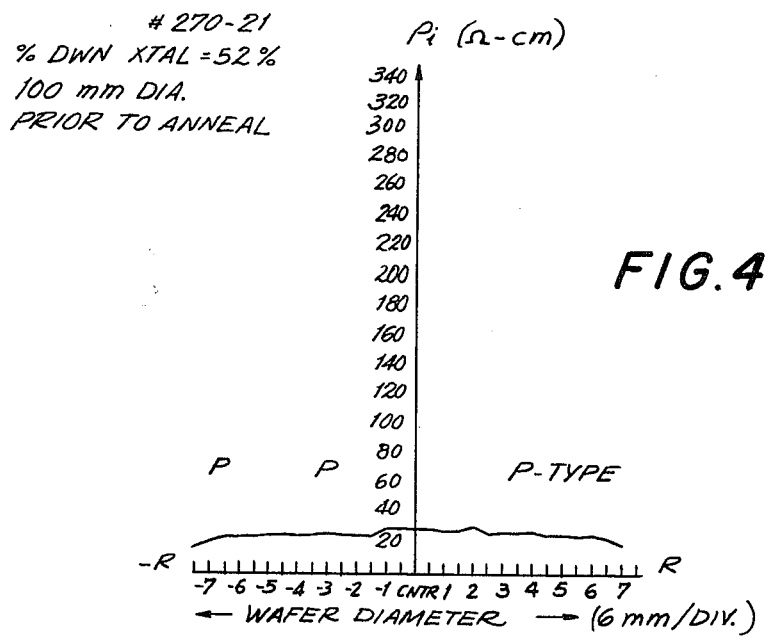
FIG. 4 is a plot similar to FIG. 1, but for a fourth sample.

Referring now to the figures of the drawing, there will be described a number of specific examples which constitute evidence of the practicability of the technique of the present invention. In particular, there will be demonstrated the predictability of the spatial variation of oxygen precipitation in a crystalline wafer based on the initial resistivity pattern; that is, whether there are observed peaks or a flat profile. More specifically, the oxygen precipitation profile will be predictable from the initial resistivity profile obtained prior to thermal donor heat treatment.

From the above cited French patent, it will be understood that although certain predictability could have been achieved in accordance with well known techniques, these always depended on, or involved, annealing heat treatment such that samples were destructively tested in order to arrive at an empirically determined precipitation rate, and to the final precipitation configuration. The present invention does not require sacrificing the sample in order to predict where the oxygen will finally precipitate.

In accordance with tests that have been made, a very high resolution resistivity mapping technique was practiced; namely, at least for the most part, a time domain reflectometry (TDR) with capacitive coupling. Such measuring technique has per se been described in *IBM Research Report RC* 6077, 6/25/76, B. J. Elliott. Also, oxygen data were collected using the well known Fourier transform infrared spectrometer. The initial resistivity scans, which provide the aforenoted profiles and which are taken prior to the thermal donor anneal, detect a compensated intrinsic region found to be coincident with an oxygen precipitation annulus (verified by infrared absorption measurements and X-ray topography after thermal processing).

Unexpectedly, and quite contrary to conclusions drawn from earlier work, it was found that the greatest amount of oxygen precipitation does not occur at the maximum of the product of interstitial oxygen and thermal donor concentrations. Earlier speculations were made without knowledge of the change in conductivity type which occurs in some wafers in going from edge to center of a wafer. Thus, the thermal donor concentration profile in this material has the expected bell shape. However, it has been found that the greatest precipitation occurs in or around the intrinsic region located between an outer p-type ring and an inner n-type disc. The material used in the various experiments came from a 100 mm. crystal grown in a conventional manner, with resistivity in the range of 11–25 ohm-cm. Four samples were chosen by means of a diagonal groove across the minor flat. The samples corresponded to normalized distances down the length of the crystal of 0.01, 0.12, 0.24 and 0.52. These four samples were chosen because they encompassed the three major resistivity forms. The three major forms are: (1) a doubly peaked profile with a p-n-p transition across the wafer diameter; (2) a singly peaked profile with a high resistivity center but p-type everywhere and (3) an essentially flat curve with relatively low resistivity but p-type everywhere.

The samples were first characterized for initial resistivity. The diameter of each was profiled using the capacitive TDR technique. Measurements were made every six millimeters. The spatial resolution of the TDR system used was less than two millimeters. These data are plotted in FIGS. 1 through 4.

The TDR technique can be thought of as a pulsed spreading resistance measurement. In this technique, a voltage step is propagated down the transmission line and is capacitively coupled to a small region of the wafer by means of a coaxial probe. The incident pulse and reflected pulse from the sample are monitored. The initial reflected amplitude is a function of the local bulk resistivity of the sample. Since these measurements were made prior to any thermal donor anneal, the resistivity values were a measure of both the intended dopant and the oxygen thermal donor complex.

Figure 5A:
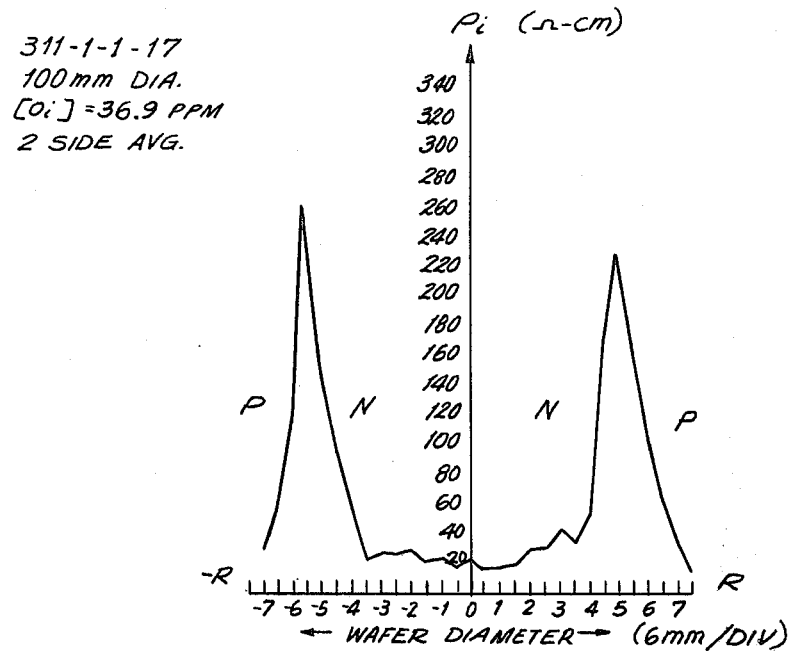
FIG. 5A is a plot similar to FIG. 1, but for a fifth sample, the measurement being made by time domain reflectometry.
Figure 5B:
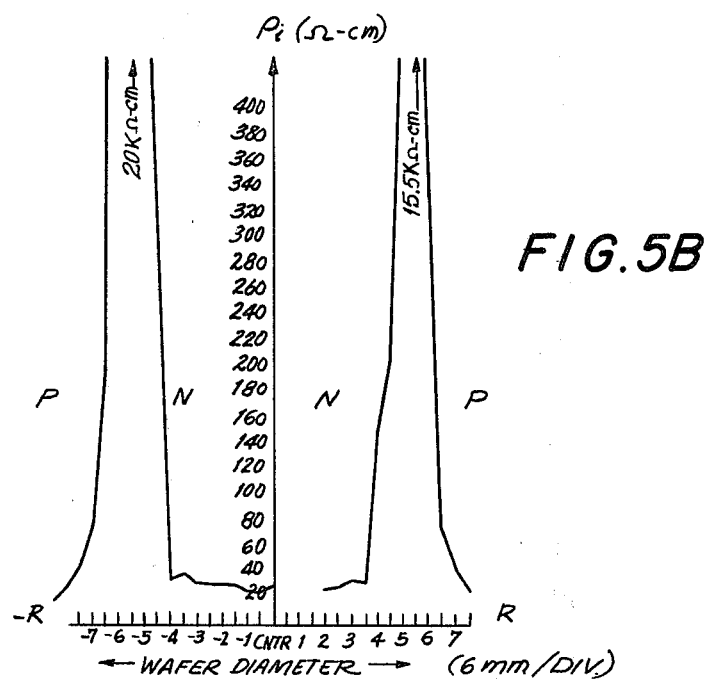
FIG. 5B is a plot for the fifth sample, but with the measurement made by a 4-point probe.

The TDR results were checked on a fifth sample by doing additional mapping with the four point probe. The TDR and four point probe results for this sample are shown in FIGS. 5A and 5B respectively. The two techniques produced the same qualitative curve shape for this sample. With the four point probe, a photo voltage effect was noted in the high resistivity regions. This led to typing of the wafers. It was found that there was a conductivity type change when going from the edge of the wafer to the center. There exists an outer p-type ring separated from an inner n-type disc by an annular intrinsic region.

Figure 6A:
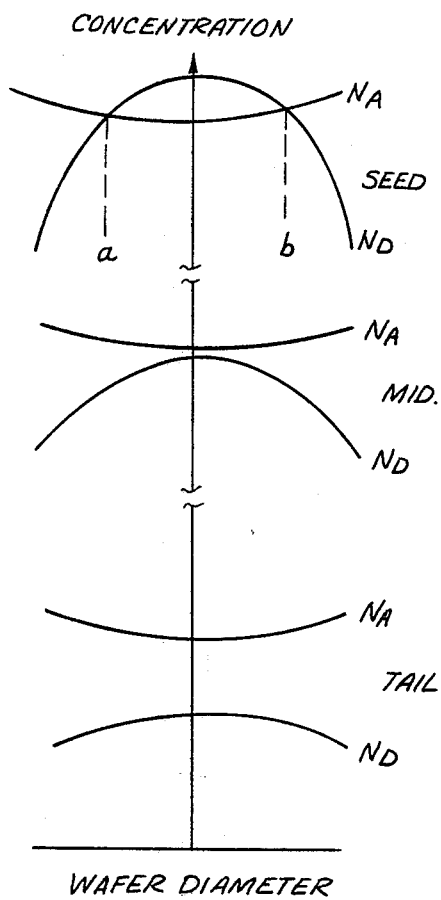
FIG. 6A is a plot illustrating the seed-to-tail variations of the concentrations of dopant ($N_A$) and thermal donors ($N_D$).

The three basic resistivity curve shapes can be explained as follows. Referring to FIG. 6A one sees that the thermal donors will compensate the intended p-type boron dopant. In the seed end of the crystal, the peak concentration of the thermal donors can exceed that of the boron. When this occurs, the material is converted to n-type. The annular intrinsic region would then be coincident with the points at which the donor and acceptor concentration were equal, points (a, b) in FIG. 6A.

Proceeding down the length of the crystal, one would find the peak concentration of the thermal donors decreasing while the acceptor concentration was increasing. Thus, the two peaks would tend to coalesce, forming a single peak in the center of the wafer without any conductivity type change.

Figure 6B:
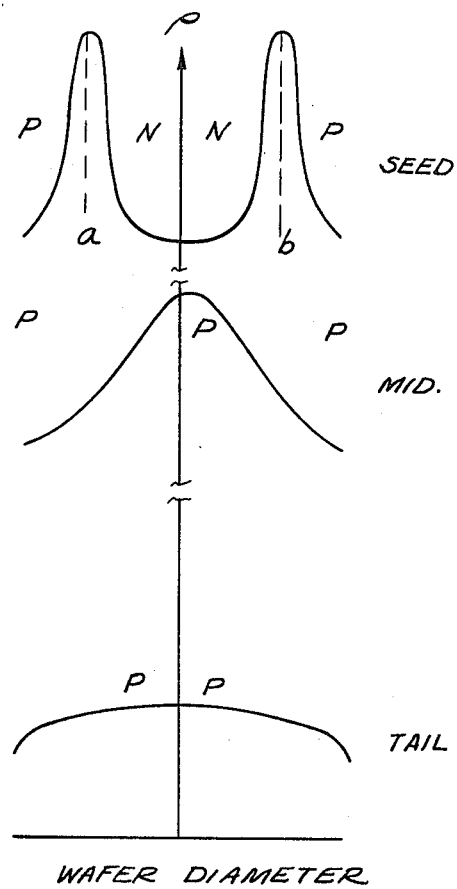
FIG. 6B is a plot illustrating the seed-to-tail variations of resistivity versus wafer diameter.

Finally, the point is reached at which the oxygen donor complex concentration is less than that of the boron. An essentially flat resistivity profile (FIG. 6B) is obtained at this point and for the remainder of the crystal. Again, the conductivity type is constant across the wafer, being p-type.

With respect to these samples, the double resistivity peak form was found for approximately the first 15% of the crystal. The flat resistivity form was reached at a point less than 50% down the crystal.

Referring now to FIGS. 7–10, the initial oxygen concentration was measured at five or six points along a radius of each sample. The measurement was made on a Fourier transform infrared spectrometer. The IR absorbance is plotted in FIGS. 7 and 8. Equivalent concentrations in parts per million are also indicated on the plots. The concentration is linearly related to the absorbance and inversely proportional to the thickness of the sample which, in this case, was about 0.7 mm (27 mils).

Before any thermal processing the oxygen concentration was fairly constant along the radius about one centimeter from the edge, at which point the concentration dropped by five to ten parts per million. The peak concentration in the center of the seed end was 40 ppm, dropping to 33 ppm by mid crystal.

These oxygen concentration profiles would be expected to generate bell shaped thermal donor concentration profiles. This would be consistent with the resistivity results discussed previously.

Figure 7:
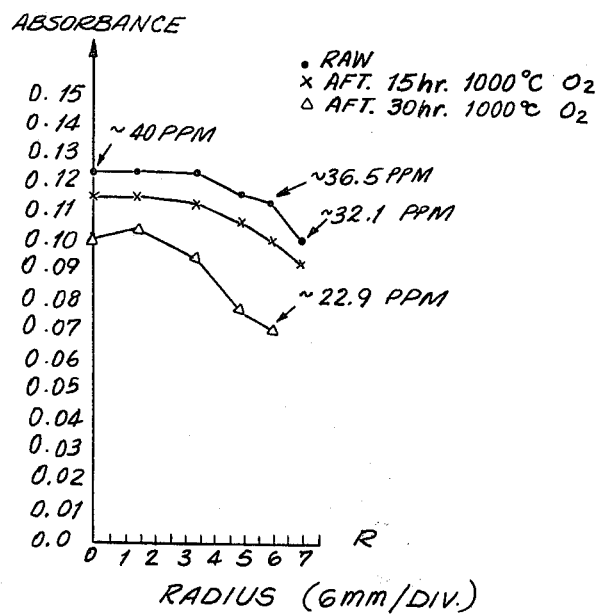
FIG. 7 is a plot of the infrared absorbance versus wafer radius for the same sample as in FIG. 1.
Figure 8:
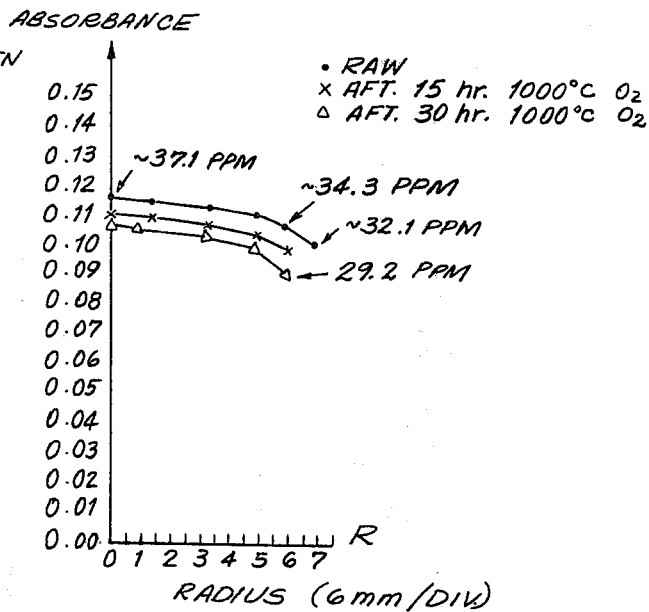
FIG. 8 is another plot of infrared absorbance versus wafer radius for the sample of FIG. 3.

Referring to FIGS. 7 and 8, two samples were subjected to thirty hours at 1000 C in two steps. Each fifteen hour step was done in a dry oxygen ambient in an MOS qualified furnace. After each oxidation, the resulting 430 nm oxide was stripped, and infrared absorption measurements were made to determine the remaining interstitial oxygen concentration. These data are plotted in FIGS. 7 and 8 along with the initial oxygen data. It will be seen in these figures that the greatest amount of precipitation occurred out near the edge of the wafer. It is easier to determine the amount of precipitation if one plots the difference, point by point, of the initial interstitial oxygen concentration and that after thirty hours of thermal processing. These data are plotted in FIGS. 9 and 10.

Figure 9:
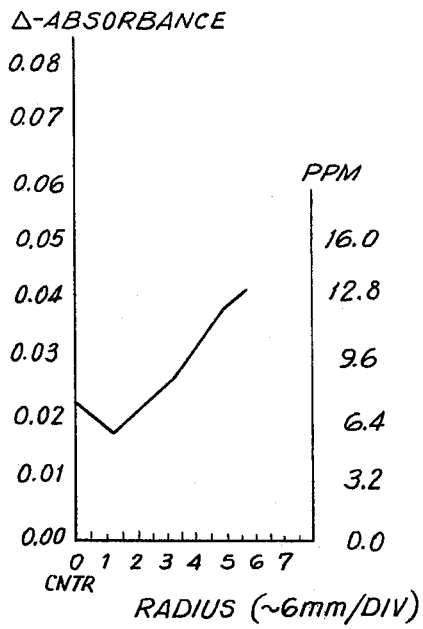
FIG. 9 is a plot of oxygen precipitation versus radius for the sample of FIG. 7.

Examining FIG. 9, we see that sample 270-1 (1% down crystal) precipitated to the greatest extent in the annular regions which were predicted by the initial resistivity profiles. A much smaller amount of precipitation occurred in sample 270-10 (24% down crystal, FIG. 10). The precipitation pattern on this sample showed little or no increase as one proceeded from center to edge. If one were to label this more uniform precipitation-characteristic as 'background', then it is obvious that this background is present in both samples and is a decreasing function of length down the crystal.

Figure 10:
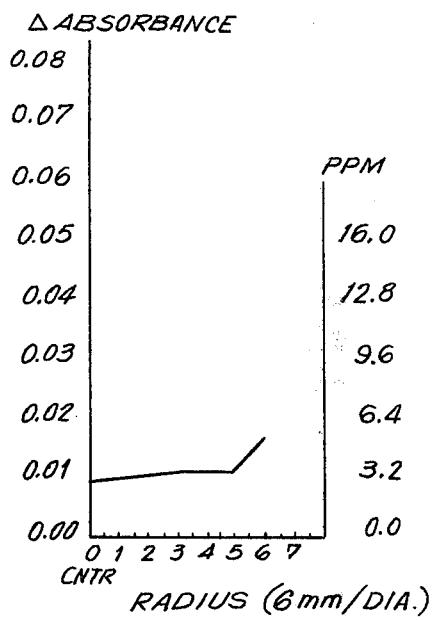
FIG. 10 is a plot of oxygen precipitation versus radius for the sample of FIG. 8.

The oxygem precipitation profile for the samples 270-1 and 270-10, depicted in FIG. 9 and FIG. 10, respectively, is the result of a particular form of heat treatment, which operates to produce the greatest extent of precipitation in the annular region defined near the edge of the wafer. It is to be noted that a totally different form of heat treatment will bring about the opposite precipitation profile to that of FIG. 9 and FIG. 10, that is, a profile having a negative slope, rather than the positive slope exhibited. Thus, the least amount of precipitation will occur in the annular region near the edge and the greatest amount everywhere else.

What has been disclosed is an efficient measurement technique for enabling characterization of semi-conductor wafers for ultimate device purposes. The technique is non-destructive in nature because it is performed on the wafers prior to any conventional annealing heat treatment; nevertheless, it yields an accurate prediction, based on initial resistivity measurements, of the final oxygen precipitation profile that will be obtained in those wafers.

While there has been shown and described what is considered at present to be the preferred embodiment of the present invention, it will be appreciated by those skilled in the art that modifications of such embodiment may be made. It is therefore desired that the invention not be limited to this embodiment, and it is intended to cover in the appended claims all such modifications as fall within the true spirit and scope of the invention.

What is claimed is:

1. A process for characterizing semiconductor wafers, which have been cut from a crystalline body for purposes of integrated circuit manufacture, comprising the steps of:

measuring, prior to any thermal treatment, the resistivity at a plurality of sites along the diameter of the wafers;

characterizing such wafers by the diametral resistivity profile thus obtained, according to which changes in oxygen preciptation can be predicted precisely where compensated intrinsic regions have been measured; and, classifying said wafers based on the predicted oxygen precipitation characterisitcs, such that wafers having a substantially uniform diametral resistivity profile can be immediately used on a conventional production line, whereas the remaining wafers can be retained for use in accordance with their predicted individual precipitation characteristics corresponding with the measured compensated intrinsic regions.

2. A process as defined in claim 1, in which an annular region at the edge of the wafers and defining the final oxygen precipitation profile, corresponds with compensated intrinsic regions measured by the first step.

3. A process as defined in claim 1, in which said semiconductor wafers are of monocrystalline silicon.

4. A process as defined in claim 1, further including the step of feeding back the resistivity information obtained by step 1 to the crystal growth operation so as to correct any predicted, undesired oxygen precipitation characteristic.

* * * * *